United States Patent [19]
Fellner et al.
[11] 4,351,948
[45] Sep. 28, 1982

[54] IMIDAZOLE HYDRAZONE DERIVATIVES

[75] Inventors: Peter J. Fellner, Marlow, England; Brendan J. Hamill, Livingston, Scotland; Paul W. Manley, High Wycombe, England

[73] Assignee: G.D. Searle & Co., Skokie, Ill.

[21] Appl. No.: 225,583

[22] Filed: Jan. 16, 1981

[30] Foreign Application Priority Data

Jan. 25, 1980 [GB] United Kingdom ................. 8002577

[51] Int. Cl.[3] .................... C07D 409/06; C07D 233/61
[52] U.S. Cl. .................................... 548/336; 424/263; 424/273 R; 546/278; 548/341
[58] Field of Search ................ 548/341, 336; 546/278; 424/273 R, 263

[56] References Cited

U.S. PATENT DOCUMENTS 3,830,642 8/1974 Moon .................................... 71/107
3,927,017 12/1975 Heeres et al. ........................ 548/341

FOREIGN PATENT DOCUMENTS 1533706 3/1976 United Kingdom .
1533705 11/1978 United Kingdom .
1533748 11/1978 United Kingdom .

OTHER PUBLICATIONS

*Chemical Abstracts*, 84:13501y (1976), [Fr. Demande 2,249,616, Thizy et al., 5/30/75].

*Primary Examiner*—Richard A. Schwartz
*Attorney, Agent, or Firm*—Albert Tockman; James G. Passe; Albin James Nelson

[57] ABSTRACT

Compounds corresponding to the following general formula:

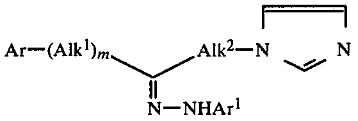

wherein

Ar and $Ar^1$, which may be the same or different, each represents an aromatic radical which may be substituted one or more times by halogen and/or nitro and/or lower alkyl and/or trihalomethyl and/or cyano and/or lower alkoxy and/or di-lower alkylamino, the alkyl groups optionally completing a ring optionally incorporating a further heteroatom, and/or lower alkyl sulphonyl;

$Alk^1$ and $Alk^2$, which may be the same or different, each represents an alkylene group containing from one to eight carbon atoms which may be substituted one or more times by aryl and/or cycloalkyl and/or lower alkyl and if two such alkyl groups are present, they may complete a ring optionally containing a heteroatom and in which imidazole ring may be further substituted; and m represents 0 or 1; provided that not both Ar and $Ar^1$ represent phenyl; and acid addition salts thereof. Such compounds are prepared by reaction of a compound corresponding to the following general formula:

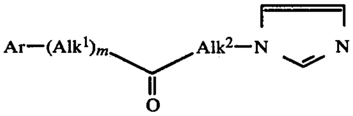

with a compound of the formula:

$Ar^1—NH—NH_2$

The compounds have an anti-fungal activity as well as an antianaerobic and anti-thrombotic activity.

17 Claims, No Drawings

IMIDAZOLE HYDRAZONE DERIVATIVES

This invention relates to imidazole hydrazone derivatives.

The present invention provides compounds corresponding to the following general formula I:

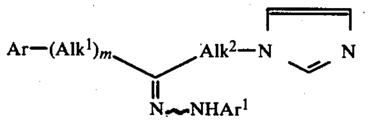

(I)

wherein

Ar and $Ar^1$, which may be the same or different, each represents an aromatic radical which may be substituted one or more times by halogen and/or nitro and/or lower alkyl and/or trihalomethyl and/or cyano and/or lower alkoxy and/or di-lower alkyl-amino, the alkyl group optionally completing a ring optionally incorporating a further heteroatom, and/or lower alkyl sulphonyl;

$Alk^1$ and $Alk^2$, which may be the same or different, each represents an akylene group containing from one to eight carbon atoms which may be substituted one or more times by aryl and/or cycloalkyl and/or lower alkyl, and if two such alkyl groups are present, they may complete a ring optionally containing a heteroatom; and in which the imidazole ring may be further substituted in particular by one or more lower alkyl groups and m represents 0 or 1; provided that not both Ar and $Ar^1$ represent phenyl; and acid addition salts thereof.

The wavy line between the C═N and $NHAr^1$ groups indicates the possibility of the isomerism. The compounds may be isolated in the form of a mixture of isomers or as the isomers themselves in particular the E and Z isomers and the invention extends to such mixtures and such isomers.

For the present purposes, the term 'lower' as used in referring to alkyl or alkoxy groups means those groups having from 1 to 7 carbon atoms.

The alkylene group represented by $Alk^1$ and $Alk^2$ preferably contains 1 to 3 carbon atoms. The imidazole group may be unsubstituted or substituted.

Certain preferred compounds according to the present invention are those wherein Ar and $Ar^1$, which may be the same or different, each represents optionally substituted phenyl, thienyl or pyridyl. (The substituents being as described above). Preferred substituents in this context include halogen and/or trihalomethyl and/or cyano.

In one preferred case, $Alk^2$ represents $—CH_2—$ and m represents 0.

Examples of specific groups falling within the above definition of Ar and $Ar^1$ include: phenyl, 2-; 3- or 4-chlorophenyl; 2,3-; 2,4-; 2,5-; 2,6-; 3,4-; or 3,5-dichlorophenyl; 2,4,6-trichlorophenyl; 2-; 3- or 4-bromophenyl; 2- or 4-fluorophenyl; 2- or 4-methylphenyl; 2- or 4-methoxyphenyl; 3-trifluoromethylphenyl, 4-cyanophenyl; 4-dimethylaminophenyl; 4-methylsulphonylphenyl; 2-thienyl; 5-chloro-2-thienyl; 2-pyridyl and 2-; 3- or 4-nitrophenyl.

Particularly preferred compounds include those wherein:

Ar represents 4-chlorophenyl and $Ar^1$ represents 2,4-dichlorophenyl;

Ar represents 4-chlorophenyl and $Ar^1$ represents 2,6-dichlorophenyl;

Ar represents 2-chlorophenyl and $Ar^1$ represents 2,4-dichlorophenyl;

Ar represents 4-chlorophenyl and $Ar^1$ represents 2,3,4,5,6-pentafluorophenyl;

Ar represents 2,4-dichlorophenyl and $Ar^1$ represents 2,4,6-trichlorophenyl;

Ar represents 4-chlorophenyl and $Ar^1$ represents 2-chlorophenyl;

Ar represents 5-chlorothien-2-yl and $Ar^1$ represents 2,6-dichlorophenyl;

and Ar represents phenyl and $Ar^1$ represents 2,4-dichlorophenyl.

Specific preferred compounds according to the invention include the following:

(E)-1-(4-chlorophenyl)-2-(1H-imidazol-1-yl)ethanone, 2,4-dichlorophenylhydrazone, hydrochloride.

(Z)-1-(4-chlorophenyl)-2-(1H-imidazol-1-yl)ethanone, 2,6-dichlorophenylhydrazone, hydrochloride.

(E)-1-(5-chlorothienyl-2-yl)-2-(1H-imidazol-1-yl)ethanone, 2,6-dichlorophenylhydrazone, hydrochloride.

(Z)-1-(4-chlorophenyl)-1-(1H-imidazol-1-yl)ethanone, 2-chlorophenylhydrazone, hydrochloride.

1-(2,4-dichlorophenyl)-2-(1H-imidazol-1-yl)ethanone, 2,4,6-trichlorophenylhydrazone, hydrochloride.

(Z)-1-(4-chlorophenyl)-2-(1H-imidazol-1-yl)ethanone, 2,3,4,5,6-pentafluorophenylhydrazone, hydrochloride.

The compounds according to the present invention may be prepared by reacting a compound corresponding to the following general formula II:

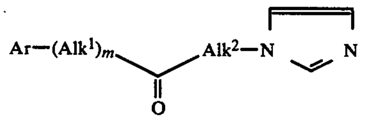

(II)

wherein

Ar, $Alk^1$, $Alk^2$ and m are as defined above; with a compound corresponding to the following general formula:

$Ar^1$—NH—$NH_2$ wherein $Ar^1$ is as defined above; the product if desired being isolated in the form of an acid addition salt, or subsequently converted from one salt to another salt.

The process is preferably carried out at an elevated temperature particularly in the presence of a solvent and an acidic catalyst. Either or both of the reactants may be used in the reaction in the form of acid addition salts.

Preferred reaction temperatures are from 20° to 100° C., advantageously from 78° to 80° C.

The nature of the solvent is not critical. Preferred solvents include methanol and ethanol.

As acid catalyst, sulphuric acid or hydrochloric acid may be used.

After reaction, the mixture may be neutralised by the addition of alkali and the product solvent-extracted and isolated by removal of the solvent. Acid addition salts of the resulting compound may be obtained if desired, by dissolving the product in a non-aqueous solvent, for example chloroform, and reacting it with a non-aqueous solution of a suitable acid.

Compounds of formula II in which m=o, a number of which have been reported in the literature, may be prepared according to the reaction scheme set out below, in which X is bromo or chloro, using methods analogous to those described in the literature, e.g., for the preparation of 1-(4-chlorophenyl-2-(1H-2-ethylimidazol-1-yl)ethanone (U.K. Pat. No. 1,244,530), and for the preparation of 1-(4-chlorophenyl)-2-(1H-imidazol-1-yl)ethanone (P. A. J. Janssen et al, J. Med. Chem., 1969, 12, 781).

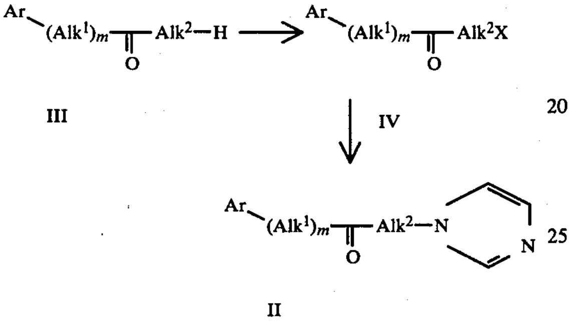

III IV II

Novel compounds of formula II, (m=0), which we have prepared are identified in the table below:

(A) Compounds in which the imidazole group is unsubstituted

| Ar | $Alk^2$ | mp(°C.) |
|---|---|---|
| 2-Br Phenyl | $CH_2$ | 191–192.5 (HCl) |
| 3-Br Phenyl | $CH_2$ | 123–124.5 |
| 2-F Phenyl | $CH_2$ | 159–160 ($HNO_3$) |
| 2,5-$Cl_2$ Phenyl | $CH_2$ | 164–168 ($HNO_3$) |
| 2,6-$Cl_2$ Phenyl | $CH_2$ | 245–247 (HCl) |
| 3,4-$Cl_2$ Phenyl | $CH_2$ | 132–134 ($HNO_3$) |
| 2-$CF_3$ Phenyl | $CH_2$ | >250 decomp (HCl) |
| 3-$CF_3$ Phenyl | $CH_2$ | 101–102 |
| 4-$CF_3$ Phenyl | $CH_2$ | 139–140 |
| 4-CN Phenyl | $CH_2$ | 214–216 ($HNO_3$) |
| 3-MeO Phenyl | $CH_2$ | 105–107 |
| 2-$NO_2$ Phenyl | $CH_2$ | 171–172 ($HNO_3$) |
| 3-$NO_2$ Phenyl | $CH_2$ | 146–149 ($HNO_3$) |
| 4-$NO_2$ Phenyl | $CH_2$ | 237–238 |
| 3-MeOOC-4-MeO Phenyl | $CH_2$ | 160–161 |
| 2-Pyridyl | $CH_2$ | 115–116 |
| 2-Naphthyl | $CH_2$ | 228–230(HCl) |
| 2-Benzofuranyl | $CH_2$ | 150–152 |
| Thien-3-yl | $CH_2$ | 143–144 (HCl) |
| 5-Br Thien-2-yl | $CH_2$ | 168–169 |
| 4,5-$Br_2$ Thien-2-yl | $CH_2$ | 185–186 |
| 2,5-$Cl_2$ Thien-3-yl | $CH_2$ | 134–135 |
| 5-Me Thien-2-yl | $CH_2$ | 126–127 |
| 4-Cl Phenyl | $CHCH_3$ | 189–190 (HCl) |
| 4-F Phenyl | $CHCH_3$ | 266–268 (HCl) |
| 4-$CF_3$ Phenyl | $CHCH_3$ | 240–242 (HCl) |
| 3,4-$Br_2$ Thien-2-yl | $CHCH_3$ | 236–238 (HCl) |
| 4,5-$Br_2$ Thien-2-yl | $CHCH_3$ | 136–138 |
| 5-Cl Thien-2-yl | $CHCH_3$ | 96–97 |
| Phenyl | CH Phenyl | Gum |
| 4-$Me_2N$ Phenyl | CH Phenyl | 125–127 (HCl) |
| 4-$Me_2N$ Phenyl | CH(4-Cl Phenyl) | Gum |
| 4-Cl Phenyl | $CHCH_2$(2,4-$Cl_2$ Phenyl | 220–222 (HCl) |
| 4-Cl Phenyl | $CHCH_2CH_2OCOCH_3$ | 101–102 |
| 4-Cl Phenyl | $CH_2CH_2$ | 165–166 (HCl) |

(B) Compounds in which the imidazole group is substituted as indicated

| Ar | Imidazole Group | $Alk^2$ | mp |
|---|---|---|---|
| 4-Br Phenyl | 2-methylimidazole | $CH_2$ | 228.5–231.5 (HCl) |
| 4-Cl Phenyl | 4-methylimidazole | $CH_2$ | 164–166 |
| 4-Cl Phenyl | 2-ethyl-4-methyl-imidazole | $CH_2$ | 141–142 |
| 4-Cl Phenyl | 2-methylimidazole | $CHCH_3$ | 263–265 (HCl) |

Compounds of formula IV in which m is 1 can be prepared by methods analogous to that described by N. Yoshida et al, Sanky Kenkyusho Nempo, 1970, 22, 89, for the preparation of 1-chloro-3-(4-chlorophenyl)propan-2-one. These compounds may then be converted to compounds of formula II as described above. By this method 1-(4-chlorophenyl)-3-(1H-imidazol-1-yl)propan-2-one was prepared, in the form of colourless needles m.p. 104°–105° C.

The compounds according to the invention have an antifungal activity. They are also active against anaerobic bacteria. They also have an antithrombotic activity.

The anti-fungal activity of the compounds is very pronounced against a wide range of pathogenic fungi, such as those of the Trichophyton species and of the Candida species and against *Epidermophyton floccosum* and *Microsporum canis.* Compared with known antifungal agents such as miconazole, econazole and clotrimazole they have the considerable and unexpected advantage of high activity when administered by the oral route. The compounds according to the invention have a toxicity which is comparable to that of the prior anti-fungal agents mentioned above but because they are more active their therapeutic index is better. Also compared with the prior known antifungal agents they are active when given by the oral route, which simplifies their administration.

The activity of the compounds against anaerobic bacteria has been demonstrated against a number of important pathogenic anaerobic bacteria such as Clostridium species, Bacteroides species and *Trichomonas vaginalis.* Like metronidazole, which is widely used at present, they are of high activity and have the advantage that they appear to be non-mutagenic in both bacterial Ames tests and mammalian cell transformation assays (Ames et al, Mutation Res., (1975), 31, 347 and McCann et al, Proc. Nat. Acad. Sci. USA, (1975), 75, 5135) whereas metronidazole is reported to be mutagenic and teratogenic. Compared with another known antianaerobic agent namely Clindamycin (trans-α-methyl-7-chloro-6,7,8-trideoxy-6-(1-methyl-4-propyl)-L-(2-pyrrolidinecarboxamido)-1-thio-L-threo-D-galacto-octopyranoside) they have the advantage of having a low toxicity. They also exhibit activity against non-pathogenic anaerobic bacteria such as *Desulfovibrio desulfuricans* which is an anaerobe present in oil wells. The use of the compounds of the invention to kill or effectively control such anaerobes is part of the present invention.

The anti-thrombotic activity of the compounds of the invention has been determined by their ability to inhibit production of thromboxane $A_2$ ($TxA_2$) by blood platelets the synthesis of which is considered to be an important factor in the aggregation of platelets and the initiation of thrombosis (R. J. Gryglewski, CRC Crit. Rev. Biochem., 1980, 7(4), 291).

Thus, there is evidence that thrombosis is determined by the balance of products derived from prostaglandin cyclic endoperoxides between the thrombogenic $TxA_2$ released on platelet aggregation and the thrombolytic prostacyclin ($PGI_2$) formed in the vessel walls. Blocking or reducing the production of $TxA_2$ is expected to be useful in the treatment and prophylaxis of thrombosis.

The active compounds are useful wherever it is desired to inhibit platelet aggregation and/or to reduce the adhesive character of platelets, and consequently to treat or prevent the formation of thrombosis in mammals, including man. For example, the compounds may be useful in the treatment and prevention of myocardial infarcts, cerebro-vascular thrombosis, ischaemic peripheral vascular disease and thrombo-embolic microangiopathy; to treat and prevent post-operative thrombosis; and to promote patency of vascular grafts following surgery.

The compounds in which the activity as an antifungal is best demonstrated are those wherein $Ar^1$ is dichlorophenyl, in particular 2,6-dichlorophenyl. The activity of the compounds as antianaerobes is best demonstrated with those compounds in $Ar^1$ is di- or tri-chloro, in particular 2,4-dichloro and 2,4,6-trichloro, also in those compounds in which $Alk^2$ has more than one carbon atom.

The compounds according to the invention may be administered by any suitable route, preferably in the form of a pharmaceutical composition adapted to such route, and in a dose effective for the treatment intended.

Accordingly the invention provides a pharmaceutical composition comprising one or more compounds according to the invention in association with one or more non-toxic, pharmaceutically acceptable carriers and/or diluents and/or adjuvants and if desired other active ingredients. The composition may for example be applied topically, orally or by injection. For topical administration, the composition may be formulated as, for example, a cream gel or ointment. Such a composition could, for example, be applied topically twice daily for a suitable period, such as two or three weeks. A suitable concentration of active ingredient in the composition could be from 1 to 5% w/w. For vaginal use, the active ingredient may be incorporated in a pessary, or a cream may be used with an applicator, or an impregnated tampon may be utilized.

For oral administration, the pharmaceutical composition may take the form of, for example, a tablet, capsule, suspension or liquid. The pharmaceutical composition is preferably made in the form of a dosage unit contained in a particular amount of the active ingredient. Examples of such dosage units are tablets or capsules. These may with advantage contain an amount of active ingredient from 5 to 250 mg preferably 25 to 150 mg. A suitable daily dose for a mammal may vary widely depending on the condition of the patient and other factors. However, a dose of from 0.1 to 300 mg/kg body weight particularly 0.5 to 10 mg/kg body weight preferably 5 mg to 10 mg/kg body weight may be appropriate.

The active ingredient may also be administered by injection as a composition wherein, for example, saline, dextrose or water for injection may be used as a suitable carrier. When used as an antithrombotic the preferred routes of administration are the oral route or by injection.

As indicated the dose administered and the treatment regimen will be dependent, for example, on the infection, the severity thereof, on the patient being treated and his response to treatment and therefore may be widely varied.

The pharmaceutical compositions may be prepared by techniques well known in the art and described, inter alia, in Remington's Pharmaceutical Science, Mach Publishing Co., Easton, Pa., 1965. The present invention is further illustrated by the following Examples.

EXAMPLE 1

E-1-(4-Chlorophenyl)-2-(1H-imidazol-1-yl)ethanone,2,4-dichlorophenylhydrazone, hydrochloride A mixture of 1-(4-chlorophenyl)-2-(1H-imidazol-1-yl)ethanone (135.5 g), 2,4-dichlorophenylhydrazine, hydrochloride (154.0 g), and hydrochloric acid (0.5 ml of 12 M) in ethanol (615 ml) was heated under reflux, with stirring, for 5 hours. On cooling the product was filtered off and recrystallised from ethanol/ethyl acetate to give (E)-1-(4-chlorophenyl)-2-(1H-imidazol-1-yl)ethanone, 2,4-dichlorophenylhydrazone, hydrochloride, m.p. 187°-188° C. (Analysis found: C, 49.14; H, 3.32; Cl, 33.84; N, 13.36. $C_{17}H_{14}Cl_4N_4$ requires: C, 49.06; H, 3.39; Cl, 34.07; N, 13.46%). NMR ($d^6$-DMSO) δ5.68 (2H, singlet), 7.2-7.9 (10H, multiplet,) 8.36 (1H, singlet), 9.29 (1H, singlet). The E-stereochemistry was confirmed by X-ray crystallographic analysis.

EXAMPLE 2

Z-1-(4-chlorophenyl)-2-(1H-imidazol-1-yl)ethanone,2,4-dichlorophenylhydrazone, hydrochloride A mixture of 1-(4-chlorophenyl)-2-(1H-imidazol-1-yl)ethanone (6.6 g) and 2,4-dichlorophenylhydrazine, hydrochloride (7.5 g) were dissolved, with stirring in ethanol (70 ml). The resulting solution was heated at 35° C. for 30 minutes and then left to cool at 0° C. for 2 hours to give (Z)-1-(4-chlorophenyl)-2-(1H-imidazol-1-yl)ethanone, 2,4-dichlorophenylhydrazone, hydrochloride, m.p. 186°-188° C. NMR ($d^6$-DMSO) δ5.98 (2H, singlet), 7.1-8.0 (10H, multiplet), 9.51 (1H, singlet), 9.63 (1H, singlet).

EXAMPLE 3

Z-1-(4-Chlorophenyl)-2-(1H-imidazol-1-yl)ethanone, 2,6-dichlorophenylhydrazone, hydrochloride To a stirred solution of 1-(4-chlorophenyl)-2-(1H-imidazol-1-yl)ethanone (33.08 g) in ethanol (400 ml) at 70° C. was added a solution of 2,6-dichlorophenylhydrazine, hydrochloride (34.16 g) in ethanol (400 ml). The mixture was heated under reflux for 6 hours, concentrated (to 250 ml) and allowed to cool. The product was filtered off and recrystallised from ethanol to give (Z)-1-(4-chlorophenyl)-2-(1H-imidazol-1-yl)ethanone, 2,6-dichlorophenylhydrazone, hydrochloride, m.p. 210°-211° C. (Analysis found: C, 49.03; H, 3.37; Cl, 33.92; N, 13.45. $C_{17}H_{14}Cl_4N_4$ requires: C, 49.06; H, 3.39; Cl, 34.08; N, 13.46%). NMR ($d^6$-DMSO) δ5.80 (2H, singlet), 7.13-7.84 (10H, multiplet), 9.22 (1H, singlet), 9.65 (1H, singlet) The Z-stereochemistry was confirmed by X-ray crystallographic analysis.

EXAMPLE 4

E-1-(4-Chlorophenyl)-2-(1H-imidazol-1-yl)ethanone, 2,6-dichlorophenylhydrazone, hydrochloride A mixture of 1-(4-chlorophenyl)-2-(1H-imidazol-1-yl)ethanone (2.61 g) and 2,6-dichlorophenylhydrazine, hydrochloride (2.77 g) in ethanol (500 ml) was heated under reflux for 120 hours. The solution was concentrated (to 30 ml) and filtered. The filtrate was further concentrated (to 5 ml) and treated dropwise with ether (200 ml). The precipitated product was filtered off and washed with ether to give (E)-1-(4-chlorophenyl)-2-(1H-imidazol-1-yl)ethanone, 2,6-dichlorophenylhydrazone, hydrochloride, as an unstable solid, m.p. 208°-9° C. (decomp.). NMR ($d^6$-DMSO) δ5.41 (2H, singlet), 6.7-7.8 (10H, multiplet), 7.99 (1H, singlet), 9.18 (1H, singlet).

EXAMPLE 5

E-1-(5-Chlorothien-2-yl)-2-(1H-imidazol-1-yl)ethanone, 2,6-dichlorophenylhydrazone, hydrochloride 1-(5-Chlorothien-2-yl)-2-(1H-imidazol-1-yl)ethanone (4.73 g) and 2,6-dichlorophenylhydrazine, hydrochloride (4.70 g) were dissolved in ethanol (160 ml) and heated under reflux for 18 hours. Toluene (160 ml) was added and the solution was concentrated (to 100 ml) and on cooling afforded (E)-1-(5-chlorothien-2-yl)-2-(1H-imidazol-1-yl)ethanone, 2,6-dichlorophenylhydrazone, hydrochloride, m.p. 186°-188° C. (Analysis found: C, 42.72; H, 2.83; N, 13.15. $C_{15}H_{12}Cl_4N_4S$ requires: C, 42.68; H, 2.87; N, 13.27%). NMR ($d^6$-DMSO) δ5.77 (2H, singlet), 7.7-8.4 (8H, multiplet), 9.30 (1H, singlet), 9.75 (1H, singlet). The E-stereochemistry was confirmed by X-ray crystallographic analysis.

EXAMPLE 6

Z-1-(5-Chlorothien-2-yl)-2-(1H-imidazol-1-yl)ethanone, 2,6-dichlorophenylhydrazone, hydrochloride (E)-1-(5-Chlorothien-2-yl)-2-(1H-imidazol-1-yl)ethanone, 2,6-dichlorophenylhydrazone, hydrochloride (2.0 g) was dissolved in methanol (30 ml) and heated under reflux for 10 minutes. 1,2-Dichloroethane (500 ml) was then added and the solution was heated under reflux for 5 hours. On cooling the solution was filtered and the filtrate was evaporated to dryness at 40° C. under reduced pressure. The residue was washed with 1,2-dichloroethane and dried at 30° C. in vacuo to give (Z)-1-(5-chlorothien-2-yl)-2-(1H-imidazol-1-yl)ethanone, 2,6-dichlorophenylhydrazone, hydrochloride, as an unstable solid, m.p. 147° C. (decomp.). NMR ($d^6$-DMSO) δ5.53 (2H, singlet), 7.0-7.9 (8H, multiplet), 8.40 (1H, singlet), 9.29 (1H, singlet).

EXAMPLE 7

E- And Z-1-(4-Chlorophenyl)-2-(1H-imidazol-1-yl)ethanone, 2,3,4,5,6-pentafluorophenylhydrazone, hydrochloride 1-(4-Chlorophenyl)-2-(1H-imidazol-1-yl)ethanone (22.0 g) and 2,3,4,5,6-pentafluorophenylhydrazine (20.0 g) were dissolved in ethanol (300 ml) containing an excess of ethereal hydrogen chloride (ca 5 ml) and heated under reflux for 15 hours. The solution was evaporated to dryness under reduced pressure and the residue was treated with saturated aqueous sodium hydrogen carbonate solution (1000 ml) and extracted with dichloromethane (3×250 ml). The combined extracts were dried over anhydrous sodium carbonate and the solvent was evaporated off under reduced pressure to give a residue which was chromatographed on silica. Elution with 5% ethanol-chloroform gave two hydrazone free-bases, each of which were dissolved in chloroform (60 ml) and acidified with ethereal hydrogen chloride. On standing the solution derived from the less polar free-base afforded (E)-1-(4-chlorophenyl)-2-(1H-imidazol-1-yl)ethanone, 2,3,4,5,6-pentafluorophenylhydrazone, hydrochloride, m.p. 160°-162° C. (Analysis found: C, 46.42; H, 2.58; N, 12.60. $C_{17}H_{11}Cl_2F_5N_4$ requires: C, 46.70; H, 2.54; N, 12.82%). NMR ($d^6$-DMSO) δ5.40 (2H, singlet), 7.4-7.8 (7H, multiplet), 8.80 (1H, singlet), 9.15 (1H, singlet). Similarly, the more polar free-base afforded (Z)-1-(4-chlorophenyl)-2-(1H-imidazol-1-yl)ethanone, 2,3,4,5,6-pentafluorophenylhydrazone, hydrochloride, m.p. 170°-172° C.

(Analysis found: C, 46.43; H, 2.60; N, 12.74. $C_{17}H_{11}Cl_2F_5N_4$ requires: C, 46.70; H, 2.54; N, 12.82%). NMR ($d^6$-DMSO) δ5.91 (2H, doublet), 7.3-7.9 (7H, multiplet), 9.28 (1H, singlet), 10.42 (1H, singlet).

EXAMPLE 8

E-1-(4-Chlorophenyl)-2-(1H-imidazol-1-yl)ethanone, 2-chlorophenylhydrazone, hydrochloride 1-(4-Chlorophenyl)-2-(1H-imidazol-1-yl)ethanone (22 g) and 2-chlorophenylhydrazine, hydrochloride (19 g) were dissolved in ethanol (300 ml) and heated under reflux for 48 hours. The solution was evaporated to dryness and the residue was treated with saturated aqueous sodium hydrogen carbonate solution (1000 ml) and extracted with dichloromethane (3×250 ml). The combined extracts were dried over anhydrous sodium carbonate and the solvent was evaporated off under reduced pressure to give a residue which was chromatographed on silica. Elution with 5% ethanol-chloroform gave the hydrazone free-base which was dissolved in chloroform (100 ml) at 60° C. and acidified with ethereal hydrogen chloride. On cooling the solution afforded (E)-1-(4-chlorophenyl)-2-(1H-imidazol-1-yl)ethanone, 2-chlorophenylhydrazone, hydrochloride, m.p. 179°-180° C.

(Analysis found: C, 53.37; H, 4.05; N, 14.86. $C_{17}H_{15}Cl_3N_4$ requires: C, 53.49; H, 3.96; N, 14.68%). NMR ($d^6$-DMSO) δ5.50 (2H, singlet), 7.1-7.9 (10H, multiplet), 8.22 (1H, singlet), 9.23 (1H, singlet).

EXAMPLE 9

Z-1-(4-Chlorophenyl)-2-(1H-imidazol-1-yl)ethanone, 2-chlorophenylhydrazone, hydrochloride (E)-1-(4-Chlorophenyl)-2-(1H-imidazol-1-yl)ethanone, 2-chlorophenylhydrazone, hydrochloride (20 g) was suspended in 1,2-dichloroethane (250 ml) and heated under reflux for 60 hours. On cooling the product was filtered off and recrystallised from cold ethanol-ether to give (Z)-1-(4-chlorophenyl)-2-(1H-imidazol-1-yl)ethanone, 2-chlorophenylhydrazone, hydrochloride, m.p. 190°-192° C. (Analysis found: C, 53.47; H, 3.95; Cl, 27.83; N, 14.83. $C_{17}H_{15}Cl_3N_4$ requires: C, 53.49; H, 3.93; Cl, 27.90; N, 14.68%). NMR ($d^6$-DMSO) δ5.85 (2H, singlet), 6.75-7.05 (1H, multiplet), 7.10-7.90 (9H, multiplet), 9.25 (1H singlet), 9.40 (1H, singlet).

EXAMPLE 10

1-(2,4-Dichlorophenyl)-2-(1H-imidazol-1-yl)ethanone, 2,4-dichlorophenylhydrazone, hydrochloride 1-(2,4-Dichlorophenyl)-2-(1H-imidazol-1-yl)ethanone (4.9 g) and 2,4-dichlorophenylhydrazine, hydrochloride (4.7 g) were dissolved in ethanol (100 ml) and heated under reflux for 18 hours. The solvent was evaporated off under reduced pressure and the residue was dissolved in chloroform (50 ml) and acidified with ethereal hydrogen chloride. The precipitated product was filtered off and recrystallised from ethanol to give 1-(2,4-dichlorophenyl)-2-(1H-imidazol-1-yl)ethanone, 2,4-dichlorophenylhydrazone, hydrochloride, m.p. 192°-194° C.

EXAMPLE 11

1-(4-Chlorophenyl)-2-(1H-imidazol-1-yl)ethanone, phenylhydrazone, hydrochloride 1-(4-Chlorophenyl)-2-(1H-imidazol-1-yl)ethanone (4.41 g) and phenylhydrazine, hydrochloride (3.20 g) were dissolved in ethanol (100 ml) and heated under reflux for 2 hours. The solvent was evaporated off under reduced pressure and the residue was recrystallised from aqueous ethanol to give 1-(4-chlorophenyl)-2-(1H-imidazol-1-yl)ethanone, phenylhydrazone, hydrochloride, m.p. 207°-208° C.

EXAMPLE 12

(a) 1-(4-Fluorophenyl)-2-(1H-imidazol-1-yl)ethanone, 2,4-dichlorophenylhydrazone, hydrochloride A mixture of 1-(4-fluorophenyl)-2-(1H-imidazol-1-yl)ethanone (4.08 g) and 2,4-dichlorophenylhydrazine, hydrochloride (4.7 g) in ethanol (100 ml) was heated under reflux for 16 hours. The solution was evaporated to dryness under reduced pressure and the residue was treated with saturated aqueous sodium hydrogen carbonate solution (100 ml) and extracted with dichloromethane (3×50 ml). The combined extracts were dried over anhydrous sodium carbonate and the solvent was evaporated off under reduced pressure to give a residue which was chromatographed on silica. Elution with 2½% ethanol-chloroform gave the hydrazone free-base which was dissolved in ether (50 ml) and acidified with ethereal hydrogen chloride. The precipitated product was filtered off and recrystallised from ethanol/ethyl acetate to give 1-(4-fluorophenyl)-2-(1H-imidazol-1-yl)ethanone, 2,4-dichlorophenylhydrazone, hydrochloride, m.p. 159°-60° C.

The following were prepared in an analogous manner:

(b) 1-(4-methylphenyl)-2-(1H-imidazol-1-yl) ethanone, 2,4-dichlorophenylhydrazone, hydrochloride, m.p. 182°-3° C.

(c) 1-(2-chlorophenyl)-2-(1H-imidazol-1-yl) ethanone, 2,4-dichlorophenylhydrazone, hydrochloride, m.p. 110°-2° C.

(d) 1-(3,4-dichlorophenyl)-2-(1H-imidazol-1-yl) ethanone, 2,4-dichlorophenylhydrazone, hydrochloride, m.p. 196°-7° C.

(e) 1-(4-nitrophenyl)-2-(1H-imidazol-1-yl) ethanone, 2,4-dichlorophenylhydrazone, hydrochloride, m.p. 137°-139° C.

EXAMPLE 13

1-(4-Methoxyphenyl)-2-(1H-imidazol-1-yl)ethanone, 2,4-dichlorophenylhydrazone, hydrochloride 1-(4-Methoxyphenyl)-2-(1H-imidazol-1-yl)ethanone (4.32 g) and 2,4-dichlorophenylhydrazine, hydrochloride (4.70 g) were dissolved in ethanol (50 ml) and heated under reflux for 16 hours. The solution was adjusted to pH 8 with saturated aqueous sodium hydrogen carbonate solution, diluted with water (200 ml) and extracted with dichloromethane (3×100 ml). The combined extracts were dried over anhydrous sodium sulphate and the solvent was evaporated off under reduced pressure to give a residue which was dissolved in ether (50 ml) and acidified with ethereal hydrogen chloride. The precipitated product was filtered off and recrystallised from ethanol/ethyl acetate to give 1-(4-methoxyphenyl)-2-(1H-imidazol-1-yl) ethanone, 2,4-dichlorophenylhydrazone, hydrochloride, m.p. 208°-209° C.

EXAMPLE 14

(a) 1-(4-Methylphenyl)-2-(1H-imidazol-1-yl) ethanone, 2,4-dinitrophenylhydrazone, hydrochloride A solution of 1-(4-methylphenyl)-2-(1H-imidazol-1-yl) ethanone (4.0 g) in ethanol (50 ml) at 70° C. was added to a solution of 2,4-dinitrophenylhydrazine (4.0 g) in methanolic sulfuric acid [50 ml of a 95% methanol—5% sulfuric acid (18 M) mixture] and heated under reflux for 16 hours. The solution was adjusted to pH 8 with saturated aqueous sodium hydrogen carbonate solution, diluted with water (200 ml) and extracted with dichloromethane (3×100 ml). The combined extracts were dried over anhydrous sodium sulphate, treated with acetone (5 ml) and allowed to stand at ambient temperature for 10 minutes. The solvent was evaporated off under reduced pressure and the residue was extracted with ether (2×50 ml). The combined extracts were filtered acidified with ethereal hydrogen chloride and the precipitated product was filtered off and recrystallised from ethanol/ethyl acetate to give 1-(4-methylphenyl)-2-(1H-imidazol-1-yl) ethanone, 2,4-dinitrophenylhydrazone, hydrochloride, m.p. 195°-196° C.

The following compounds were prepared in an analogous manner:

(b) 1-phenyl-2-(1H-imidazol-1-yl)ethanone, 2,4-dinitrophenylhydrazone, hydrochloride, m.p. 237°-9° C.

(c) 1-(4-chlorophenyl)-2-(1H-imidazol-1-yl) ethanone, 2,4-dinitrophenylhydrazone, hydrochloride m.p. 219°-21° C.

(d) 1-(4-bromophenyl)-2-(1H-imidazol-1-yl) ethanone, 2,4-dinitrophenylhydrazone, hydrochloride, m.p. 235°-6° C.

(e) 1-(4-fluorophenyl)-2-(1-imidazol-1-yl) ethanone, 2,4-dinitrophenylhydrazone, hydrochloride, m.p. 218°-20° C.

(f) 1-(4-methoxyphenyl)-2-(1H-imidazol-1-yl) ethanone, 2,4-dinitrophenylhydrazone, hydrochloride, m.p. 223°-5° C.

(g) 1-(2-chlorophenyl)-2-(1H-imidazol-1-yl) ethanone, 2,4-dinitrophenylhydrazone, hydrochloride, m.p. 227°-9° C.

(h) 1-(2,4-dichlorophenyl)-2-(1H-imidazol-1-yl)ethanone, 2,4-dinitrophenylhydrazone, hydrochloride, m.p. 211°-3° C.

(i) 1-(3,4-dichlorophenyl)-2-(1H-imidazol-1-yl) ethanone, 2,4-dinitrophenylhydrazone, hydrochloride, m.p. 286°-8° C.

(j) 1-(4-nitrophenyl)-2-(1H-imidazol-1-yl) ethanone, 2,4-dinitrophenylhydrazone, hydrochloride, m.p. 235°-8° C.

EXAMPLE 15

(a) 1-(4-Chlorophenyl)-2-(1H-imidazol-1-yl)ethanone, 4-chlorophenylhydrazone, hydrochloride 1(4-Chlorophenyl)-2-(1H-imidazol-1-yl)ethanone (4.41 g) and 4-chlorophenylhydrazine, hydrochloride (4.0 g) were dissolved in ethanol (100 ml) and heated under reflux for 16 hours. The solution was evaporated to dryness under reduced pressure and the residue was treated with saturated aqueous sodium hydrogen carbonate solution (100 ml) and extracted with chloroform (3×50 ml). The combined extracts were dried over anhydrous sodium sulphate and the solvent was evaporated off under reduced pressure to give a residue which was dissolved in ether (50 ml), filtered and acidified with ethereal hydrogen chloride. The precipitated product was filtered off and recrystallised from ethanol ethyl acetate to give 1-(4-chlorophenyl)-2-(1H-imidazol-1-yl)ethanone, 4-chlorophenylhydrazone, hydrochloride, m.p. 200°-201° C.

The following were prepared in an analogous manner:

(b) 1-(4-chlorophenyl)-1-(1H-imidazol-1-yl) ethanone, 2-chlorophenylhydrazone, hydrochloride, m.p. 185°-6° C.

(c) 1-(4-chlorophenyl)-2-(1H-imidazol-1-yl) ethanone, 3-chlorophenylhydrazone, hydrochloride, m.p. 209°-210° C.

(d) 1-(4-chlorophenyl)-2-(1H-imidazol-1-yl) ethanone, 2-3-dichlorophenylhydrazone, hydrochloride, m.p. 200°-201° C.

(e) 1-(4-chlorophenyl)-2-(1H-imidazol-1-yl) ethanone, 2,5-dichlorophenylhydrazone, hydrochloride, m.p. 198°-9° C.

EXAMPLE 16

(a) 1-(4-Chlorophenyl)-2-(1H-imidazol-1-yl) ethanone, 3,4-dichlorophenylhydrazone 1-(4-Chlorophenyl)-2-(1H-imidazol-1-yl)ethanone (4.41 g) and 3,4-dichlorophenylhydrazine, hydrochloride (4.80 g) were dissolved in ethanol (50 ml) and heated under reflux for 16 hours. The solution was adjusted to pH 8 with saturated aqueous sodium hydrogen carbonate solution and diluted with water (200 ml). The precipitated product was filtered off and recrystallised from aqueous ethanol to give 1-(4-chlorophenyl)-2-(1H-imidazol-1-yl)ethanone, 3,4-dichlorophenylhydrazone, m.p. 207°-8° C.

The following was prepared in an analogous manner:

(b) 1-(4-chlorophenyl)-2-(1H-imidazol-1-yl) ethanone, 3,5-dichlorophenylhydrazone, m.p. 207°-8° C.

EXAMPLE 17

1-(2-chlorophenyl)-2-(1H-imidazol-1-yl)ethanone (0.22 g) and 2,6-dichlorophenylhydrazine, hydrochloride (0.22 g) were dissolved in ethanol (50 ml) and heated under reflux for 18 hours. The solution was evaporated to dryness under reduced pressure and the residue was treated with saturated aqueous sodium hydrogen carbonate solution (100 ml) and extracted with dichloromethane (3×50 ml). The combined extracts were dried over anhydrous sodium carbonate and the solvent was evaporated off under reduced pressure to give a residue which was chromatographed on silica. Elution with chloroform gave the hydrazone free-base which was dissolved in chloroform (25 ml) and treated with ethereal hydrogen chloride to give 1-(2-chlorophenyl)-2-(1H-imidazol-1-yl)ethanone, 2,6-dichlorophenylhydrazone, hydrochloride m.p. 179°-180° C.

EXAMPLE 18

1-Phenyl-2-(1H-imidazol-1-yl)ethanone (0.19 g) and 2,6-dichlorophenylhydrazine, hydrochloride (0.22 g) were dissolved in ethanol (50 ml) and heated under reflux for 15 hours. Toluene (50 ml) was added and the solution was concentrated to half-volume. On cooling the solution afforded a colourless crystalline solid which was filtered off and recrystallised from ethanol/toluene to give 1-phenyl-2-(1H-imidazol-1-yl)ethanone, 2,6-dichlorophenylhydrazone, hydrochloride, m.p. 189°-190° C.

EXAMPLE 19

1-(2,4-Dichlorophenyl)-2-(1H-imidazol-1-yl) ethanone (0.30 g) and 2,6-dichlorophenylhydrazine, hydrochloride (0.22 g) were dissolved in ethanol (50 ml) and heated under reflux for 18 hours. The solution was evaporated to dryness under reduced pressure and the residue was treated with saturated aqueous sodium hydrogen carbonate solution (100 ml) and extracted with dichloromethane (3×50 ml). The combined extracts were dried over anhydrous sodium carbonate and the solvent was evaporated off under reduced pressure to give a residue which was chromatographed on silica. Elution with chloroform gave the hydrazone free-base which was dissolved in chloroform (25 ml), acidified with ethereal hydrogen chloride, heated to 60° C. and treated with dry toluene until turbid. On cooling the solution afforded 1-(2,4-dichlorophenyl)-2-(1H-imidazol-1-yl)ethanone, 2,6-dichlorophenylhydrazone, hydrochloride m.p. 209°-210° C.

EXAMPLE 20

1-(3-Nitrophenyl)-2-(1H-imidazol-1-yl)ethanone (0.54 g) and 2,6-dichlorophenylhydrazine, hydrochloride (0.43 g) were dissolved in ethanol (50 ml) and heated under reflux for 6 hours. Toluene (50 ml) was added and the solution was concentrated to half-volume. On cooling the solution afforded a pale yellow crystalline solid which was filtered off and recrystallised from ethanol)toluene to give 1-(3-nitrophenyl)-2-(1H-imidazol-1-yl)ethanone, 2,6-dichlorophenylhydrazone, hydrochloride m.p. 178°-180° C.

EXAMPLE 21

1-(4-Cyanophenyl)-2-(1H-imidazol-1-yl)ethanone (2.33 g) and 2,6-dichlorophenylhydrazine, hydrochloride (2.14 g) were dissolved in ethanol (100 ml) and heated under reflux for 15 hours. The solution was concentrated to half-volume and on cooling afforded 1-(4-cyanophenyl)-2-(1H-imidazol-1-yl)ethanone, 2,6-dichlorophenylhydrazone, hydrochloride m.p. 217°-219° C.

EXAMPLE 22

1-(2-Fluorophenyl)-2-(1H-imidazol-1-yl)ethanone (2.0 g) and 2,4-dichlorophenylhydrazine, hydrochloride (2.2 g) were dissolved in ethanol (100 ml) and heated under reflux for 15 hours. The solvent was evaporated off under reduced pressure and the residue was treated with saturated aqueous sodium hydrogen carbonate solution (200 ml) and extracted with dichloromethane (3×100 ml). The combined extracts were dried over anhydrous sodium carbonate and the solvent was evaporated off under reduced pressure to give a residue which was chromatographed on silica. Elution with chloroform gave the hydrazone free-base which was dissolved in dichloromethane (100 ml) and acidified with ethereal hydrogen chloride. The solvent was evaporated off under reduced pressure and the residue was recrystallised from dichloromethane/benzene to give 1-(2-fluorophenyl)-2-(1H-imidazol-1-yl)ethanone, 2,4-dichlorophenylhydrazone, hydrochloride, m.p. 166°-168° C.

EXAMPLE 23

1-(4-Chlorophenyl)-2-(1H-imidazol-1-yl)ethanone (2.20 g) and 2-bromophenylhydrazine, hydrochloride (2.23 g) were dissolved in ethanol (100 ml) and heated under reflux for 12 hours. The solution was evaporated to dryness under reduced pressure and the residue was treated with saturated aqueous sodium hydrogen carbonate solution (100 ml) and extracted with dichloromethane (3×50 ml). The combined extracts were dried over anhydrous sodium carbonate and the solvent was evaporated off under reduced pressure to give a residue which was chromatographed on silica. Elution with chloroform gave the hydrazone free-base as an oil which was dissolved in chloroform (25 ml). The solution was acidified with ethereal hydrogen chloride heated to 60° C. and treated with dry benzene until turbid. On cooling the solution afforded colourless needles of 1-(4-chlorophenyl)-2-(1H-imidazol-1-yl)ethanone, 2-bromophenylhydrazone, hydrochloride, m.p. 180°-181° C.

EXAMPLE 24

(a) 1-(4-bromophenyl)-2-(1H-imidazol-1-yl) ethanone, 2,4-dichlorophenylhydrazone, hydrochloride 1-(4-Bromophenyl)-2-(1H-imidazol-1-yl)ethanone (0.53 g) and 2,4-dichlorophenyl hydrazine, hydrochloride (0.43 g) were dissolved in ethanol (50 ml) and heated at reflux for 12 hours. The solution was evaporated to dryness under reduced pressure and the residue was treated with saturated aqueous sodium hydrogen carbonate solution (100 ml) and extracted with dichloromethane (3×50 ml). The combined extracts were dried over anhydrous sodium carbonate and the solvent was evaporated off under reduced pressure to give a residue which was chromatographed on silica. Elution with 5% ethanol/chloroform gave the hydrazone free-base as an oil which was dissolved in chloroform (25 ml). The solution was acidified with ethereal hydrogen chloride and on standing afforded colourless crystals of 1-(4-bromophenyl)-2-(1H-imidazol-1-yl)ethanone, 2,4-dichlorophenylhydrazone, hydrochloride, m.p. 169°-172° C.

The following compounds were prepared in an analogous manner:

(b) 1-Phenyl-2-(1H-imidazol-1-yl)ethanone, 2,4-dichlorophenylhydrazone, hydrochloride, m.p. 180°-182° C.

(c) 1-(2-nitrophenyl)-2-(1H-imidazol-1-yl) ethanone, 2,4-dichlorophenylhydrazone, hydrochloride, m.p. 200°-201° C.

(d) 1-(2,4-dichlorophenyl)-2-(1H-imidazol-1-yl) ethanone, 2,4-dichlorophenylhydrazone, hydrochloride, m.p. 192°-194° C.

(e) 1-(5-chlorothien-2-yl)-2-(1H-imidazol-1-yl) ethanone, 2,4-dichlorophenylhydrazone, hydrochloride, m.p. 183°-185° C.

(f) 1(4-chlorophenyl)-2-(1H-imidazol-1-yl) propanone, 2,4-dichlorophenylhydrazone, hydrochloride, m.p. 114°-116° C.

(g) 1-(2,5-dichlorophenyl)-2-(1H-imidazol-1-yl) ethanone, 2,4-dichlorophenylhydrazone, hydrochloride, m.p. 205°-208° C.

(h) 1-(2-methoxyphenyl)-2-(1H-imidazol-1-yl) ethanone, 2,4-dichlorophenylhydrazone, hydrochloride, m.p. 167°-168° C.

(i) 1-(4-chlorophenyl)-2-(1H-2-methylimidazol-1-yl) ethanone, 2,4-dichlorophenylhydrazone, hydrochloride, m.p. 204°-205° C.

(j) 1-(4-chlorophenyl)-2-(1H-2-ethyl-4-methylimidazol-1-yl)ethanone, 2,4-dichlorophenylhydrazone, hydrochloride, m.p. 190°-192° C.

(k) 1-(4-chlorophenyl)-2-(1H-2-methylimidazol-1-yl) propan-1-one, 2,4-dichlorophenylhydrazone, hydrochloride, m.p. 188°-190° C.

(l) 1-(5-chlorothien-2-yl)-2-(1H-2-methylimidazol-1-yl)propan-1-one, 2,4-dichlorophenylhydrazone, hydrochloride, m.p. 180°-182° C.

(m) 1-(4-chlorophenyl)-2-(1H-2-ethylimidazol-1-yl)ethanone, 2,4-dichlorophenylhydrazone, hydrochloride, m.p. 202°-204° C.

(n) 1-(4-Chlorophenyl)-2-(1H-3-methylimidazol-1-yl)ethanone, 2,4-dichlorophenylhydrazone, hydrochloride, m.p. 189°-191° C.

EXAMPLE 25

(a)

1-(5-bromothien-2-yl)-2-(1H-imidazol-1-yl)ethanone, 2,6-dichlorophenylhydrazone, hydrochloride 1-(5-Bromothien-2-yl)-2-(1H-imidazol-1-yl)ethanone (2.71 g) and 2,6-dichlorophenylhydrazine, hydrochloride (2.13 g) were dissolved in ethanol (100 ml) and heated under reflux for 24 hours. Toluene (100 ml) was added and the solution was concentrated to half-volume and then heated under reflux for a further 24 hours. The solution was evaporated to dryness under reduced pressure and the residue was treated with saturated aqueous sodium hydrogen carbonate solution (100 ml) and extracted with dichloromethane (3×50 ml). The combined extracts were dried over anhydrous sodium carbonate and the solvent was evaporated off under reduced pressure to give a residue which was chromatographed on silica. Elution with chloroform gave the hydrazone free-base which was dissolved in chloroform (25 ml) and acidified with ethereal hydrogen chloride. On standing the solution afforded pale-yellow crystals of 1-(5-bromothien-2-yl)-2-(1H-imidazol-1-yl)ethanone, 2,5-dichlorophenylhydrazone, hydrochloride m.p. 191°-195° C.

The following compounds were prepared in an analogous manner:

(b) 1-(2,5-dichlorothien-2-yl)-2-(1H-imidazol-1-yl)ethanone, 2,6-dichlorophenylhydrazone, hydrochloride, m.p. 194°-195° C.

(c) 1-(4-bromophenyl)-2-(1H-imidazol-1-yl)ethanone, 2,6-dichlorophenylhydrazone, hydrochloride, m.p. 209°-210° C.

(d) 1-(2-fluorophenyl)-2-(1H-imidazol-1-yl)ethanone, 2,6-dichlorophenylhydrazone, hydrochloride, m.p. 177°-178° C.

(e) 1-(4-methoxyphenyl)-2-(1H-imidazol-1-yl)ethanone, 2,6-dichlorophenylhydrazone, hydrochloride, m.p. 192°-194° C.

(f) 1-(4-chlorophenyl)-2-(1H-imidazol-1-yl)propanone, 2,6-dichlorophenylhydrazone, hydrochloride, m.p. 138°-140° C.

(g) 1-(3-carbomethoxy-4-methoxy)-2-(1H-imidazol-1-yl)ethanone, 2,6-dichlorophenylhydrazone, hydrochloride, m.p. 170°-172° C.

(h) 1-(2-methylphenyl)-2-(1H-imidazol-1-yl)ethanone, 2,6-dichlorophenylhydrazone, hydrochloride, m.p. 190° C.

(i) 1-(4-methylphenyl)-2-(1H-imidazol-1-yl)ethanone, 2,6-dichlorophenylhydrazone, hydrochloride, m.p. 184°-195° C.

(j) 1-(2-nitrophenyl)-2-(1H-imidazol-1-yl)ethanone, 2,6-dichlorophenylhydrazone, hydrochloride, m.p. 192°-194° C.

(k) 1-(2-trifluoromethylphenyl)-2-(1H-imidazol-1-yl)ethanone, 2,6-dichlorophenylhydrazone, hydrochloride, m.p. 206°-210° C.

(l) 1-(4-trifluoromethylphenyl)-2-(1H-imidazol-1-yl)ethanone, 2,6-dichlorophenylhydrazone, hydrochloride, m.p. 177°-178° C.

(m) 1-(3-trifluoromethylphenyl)-2-(1H-imidazol-1-yl)ethanone, 2,6-dichlorophenylhydrazone, hydrochloride m.p. 198°-200° C.

(n) 1-(4-chlorophenyl)-4-(1H-imidazol-1-yl)propan-2-one, 2,6-dichlorophenylhydrazone, hydrochloride m.p. 150°-152° C.

EXAMPLE 26

(a) 1-(4-methoxyphenyl)-2-(1H-imidazol-1-yl)ethanone, 2,5-dichlorophenylhydrazone, hydrochloride 1-(4-Methoxyphenyl)-2-(1H-imidazol-1-yl)ethanone (2.16 g) and 2,5-dichlorophenylhydrazone, hydrochloride (2.14 g) were dissolved in ethanol (50 ml) and heated at reflux for 18 hours. The solution was evaporated to dryness under reduced pressure and the residue was treated with saturated aqueous sodium hydrogen carbonate solution (100 ml) and extracted with dichloromethane (3×50 ml). The combined extracts were dried over anhydrous sodium carbonate and the solvent was evaporated off under reduced pressure. The residue was dissolved in dichloromethane (20 ml) and acidified with ethereal hydrogen chloride. The solvent was evaporated off under reduced pressure and the residue was recrystallised from ethanol/ether to give 1-(4-methoxyphenyl)-2-(1H-imidazol-1-yl)ethanone, 2,5-dichlorophenylhydrazone, hydrochloride, m.p. 181°-183° C.

The following compounds were prepared in an analogous manner:

(b) 1-(2-chlorophenyl)-2-(1H-imidazol-1-yl)ethanone, 2,5-dichlorophenylhydrazone, hydrochloride m.p. 196°-197° C.

(c) 1-(4-cyanophenyl)-2-(1H-imidazol-1-yl)ethanone, 2,5-dichlorophenylhydrazone, hydrochloride, m.p. 195°-197° C.

(d) 1-(2-fluorophenyl)-2-(1H-imidazol-1-yl)ethanone, 2,5-dichlorophenylhydrazone, hydrochloride, m.p. 131°-133° C.

(e) 1-(4-fluorophenyl)-2-(1H-imidazol-1-yl)ethanone, 2,5-dichlorophenylhydrazone, hydrochloride, m.p. 172°-174° C.

(f) 1-(2-methylphenyl)-2-(1H-imidazol-1-yl)ethanone, 2,5-dichlorophenylhydrazone, hydrochloride, m.p. 220°-221° C.

EXAMPLE 27

(a) 1-phenyl-2-(1H-imidazol-1-yl)ethanone, 3,4-dichlorophenylhydrazone, hydrochloride 1-Phenyl-2-(1H-imidazol-1-yl)ethanone (2.14 g) and 3,4-dichlorophenylhydrazone, hydrochoride (1.86 g) were dissolved in ethanol (50 ml) and heated under reflux for 16 hours. The solution was evaporated to dryness under reduced pressure and the residue was treated with saturated aqueous sodium hydrogen carbonate solution (100 ml) and extracted with dichloromethane (3×50 ml). The combined extracts were dried over anhydrous sodium carbonate and the solvent was evaporated off under reduced pressure. The residue was dissolved in dichloromethane (50 ml) and acidified with ethereal hydrogen chloride. The solvent was evaporated off under reduced pressure and the residue was recrystallised from ethanol/ether to give 1-phenyl-2-(1H-imidazol-1-yl)ethanone, 3,4-dichlorophenylhydrazone, hydrochloride, m.p. 193°-194° C.

The following compounds were prepared in an analogous manner:

(b) 1-(4-bromophenyl)-2-(1H-imidazol-1-yl)ethanone, 3,4-dichlorophenylhydrazone, hydrochloride, m.p. 195°-196° C.

(c) 1-(4-cyanophenyl-2-(1H-imidazol-1-yl)ethanone, 3,4-dichlorophenylhydrazone, hydrochloride, m.p. 212° C.

(d) 1-(4-fluorophenyl)-2-(1H-imidazol-1-yl)ethanone, 3,4-dichlorophenylhydrazone, hydrochloride, m.p. 200°-202° C.

EXAMPLE 28

(a) 1-(2,4-dichlorophenyl)-2-(1H-imidazol-1-yl)ethanone, 2,4,6-trichlorophenylhydrazone, hydrochloride 1-(2,4-Dichlorophenyl)-2-(1H-imidazol-1-yl)ethanone (2.55 g) and 2,4,6-trichlorophenylhydrazone (2.20 g) were dissolved in ethanol (100 ml) containing saturated ethereal hydrogen chloride (1 ml) and heated under reflux for 8 hours. Toluene (100 ml) was added and the solution was concentrated to half-volume and then heated under reflux for a further 8 hours. The solution was evaporated to dryness under reduced pressure and the residue was treated with saturated aqueous sodium hydrogen carbonate solution (100 ml) and extracted with dichloromethane (3×50 ml). The combined extracts were dried over anhydrous sodium carbonate and the solvent was evaporated off under reduced pressure to give a residue which was chromatographed on silica. Elution with chloroform gave the hydrazone free-base which was dissolved in chloroform (25 ml), and acidified with ethereal hydrogen chloride, heated to 60° C. and treated with dry benzene until turbid. On cooling the solution afforded 1-(2,4-dichlorophenyl)-2-(1H-imidazol-1-yl)ethanone, 2,4,6-trichlorophenylhydrazone, hydrochloride, m.p. 206°-207° C.

The following were prepared in an analogous manner:

(b) 1-(4-chlorophenyl)-2-(1H-imidazol-1-yl)ethanone, 2,4,6-trichlorophenylhydrazone, hydrochloride, m.p. 156°-157° C.

(c) 1-(2-chlorophenyl)-2-(1H-imidazol-1-yl)ethanone, 2,4,6-trichlorophenylhydrazone, hydrochloride, m.p. 196°-198° C.

(d) 1-(4-trifluoromethylphenyl)-2-(1H-imidazol-1-yl)ethanone, 2,4,6-trichlorophenylhydrazone, hydrochloride, m.p. 104°-106° C.

(e) 1-(4-chlorophenyl)-2-(1H-imidazol-1-yl)propanone, 2,4,6-trichlorophenylhydrazone, hydrochloride, m.p. 169°-171° C.

(f) 1-(5-chlorothien-2-yl)-2-(1H-imidazol-1-yl)ethanone, 2,4,6-trichlorophenylhydrazone, hydrochloride, m.p. 129°-130° C.

(g) 1-phenyl-2-(1H-2-methylimidazol-1-yl)ethanone, 2,4,6-trichlorophenylhydrazone, hydrochloride, m.p. 142°-145° C.

EXAMPLE 29

1-(4-chlorophenyl)-3-(2,4-dichlorophenyl)-2-(1H-imidazol-1-yl)propanone, 4-chlorophenylhydrazone, hydrochloride 1-(4-chlorophenyl)-3-(2,4-dichlorophenyl)-2-(1H-imidazol-1-yl)propanone, hydrochloride (2.08 g) and 4-chlorophenylhydrazine, hydrochloride (1.07 g) was dissolved in ethanol (50 ml) and heated under reflux for 15 hours. The solution was evaporated to dryness under reduced pressure and the residue was recrystallised from ethanol to give 1-(4-chlorophenyl)-3-(2,4-dichlorophenyl)-2-(1H-imidazol-1-yl)propanone, 4-chlorophenylhydrazone, hydrochloride, m.p. 154°-155° C.

EXAMPLE 30

2-(4-chlorophenyl)-1-(4-dimethylaminophenyl)-2-(1H-imidazol-1-yl)ethanone, 2,4-dichlorophenylhydrazone, hydrochloride 2-(4-Chlorophenyl)-1-(4-dimethylaminophenyl)-2-(1H-imidazol-1-yl)ethanone, hydrochloride (0.20 g) and 2,4-dichlorophenylhydrazine, hydrochloride (0.11 g) were dissolved in ethanol (50 ml) and heated at reflux for 15 hours. The solution was evaporated to dryness under reduced pressure and the residue was treated with saturated aqueous sodium hydrogen carbonate solution (100 ml) and extracted with ethyl acetate (3×50 ml). The combined extracts were dried over anhydrous sodium carbonate and the solvent was evaporated off under reduced pressure to give a residue which was chromatographed on silica. Elution with chloroform gave the hydrazone free-base as an oil which was dissolved in dry ether and treated with ethereal hydrogen chloride to precipitate 2-(4-chlorophenyl)-1-(4-dimethylaminophenyl)-2-(1H-imidazol-1-yl)ethanone, 2,4-dichlorophenylhydrazone, hydrochloride, m.p. 155°-157° C.

EXAMPLE 31

1-(2-fluorophenyl)-2-(1H-imidazol-1-yl)ethanone 2,3-dichlorophenylhydrazine, hydrochloride 1-(2-fluorophenyl)-2-(1H-imidazol-1-yl)ethanone (2.67 g) and 2,3-dichlorophenylhydrazine, hydrochloride (2.14 g) were dissolved in ethanol (50 ml) and heated under reflux for 16 hours. The solution was evaporated to dryness under reduced pressure and the residue was treated with saturated aqueous sodium hydrogen carbonate solution (100 ml) and extracted with dichloromethane (3×50 ml). The combined extracts were dried over anhydrous sodium carbonate and the solvent was evaporated off under reduced pressure. The residue was dissolved in dichloromethane (50 ml) and acidified with ethereal hydrogen chloride. The solvent was evaporated off under reduced pressure and the residue was recrystallised from ethanol to give 1-(2-fluorophenyl)-2-(1H-imidazol-1-yl)ethanone, 2,3-dichlorophenylhydrazone, hydrochloride, m.p. 197°-198° C.

Other compounds which have been prepared by methods analogous to those described above are identified in the table below:

TABLE I

TABLE I-continued

| $Alk^1$ | $Alk^2$ | m | Ar | $Ar^1$ | m.p. (°C.) |
|---|---|---|---|---|---|
| — | $CH_2$ | 0 | 4-Cl phenyl | 4-Br phenyl | 199-200 (HCl) |
| — | $CH_2$ | 0 | 4-Cl phenyl | 4-CN phenyl | 186-7 (HCl) |
| — | $CH_2$ | 0 | 4-$NO_2$ phenyl | 2,6-$Cl_2$ phenyl | 180-2 (HCl) |
| — | $CH_2$ | 0 | 4-F phenyl | 2,6-$Cl_2$ phenyl | 181-3 (HCl) |
| — | $CH_2$ | 0 | 4-Cl phenyl | Pyrid-2-yl | 235-7 (2HCl) |
| — | $CH_2$ | 0 | 4-CN phenyl | 2,4-$Cl_2$ phenyl | 190-191 (HCl) |
| — | CH (phenyl) | 0 | 4-$Me_2N$ phenyl | 2,4-$Cl_2$ phenyl | 124 (HCl) |
| — | $CH_2$ | 0 | 5-Cl Thien-2-yl | 3,4-$Cl_2$ phenyl | 180-1 (HCl) |
| — | $CH_2$ | 0 | 4-Me phenyl | 2,4,6-$Cl_3$ phenyl | 172-4 (HCl) |
| — | $CH_2$ | 0 | 4-CN phenyl | 2,4,6-$Cl_3$ phenyl | 183-5 (HCl) |
| — | $CH_2$ | 0 | 4-F phenyl | 2,4,6-$Cl_3$ phenyl | 165-7 (HCl) |
| — | $CH_2$ | 0 | 4-Cl phenyl | 2,3,5,6-$F_4$ phenyl | 210-12 (HCl) |
| — | $CH_2$ | 0 | 4-$NO_2$ phenyl | 2-Cl phenyl | 202-5 (HCl) |
| — | $CH_2$ | 0 | 4-$NO_2$ phenyl | 2,3,5,6-$F_4$ phenyl | 196-8 (HCl) |
| — | $CH_2$ | 0 | 4-$NO_2$ phenyl | 2,3,4,5,6-$F_5$ phenyl | 179-180 (HCl) |
| — | $CH_2$ | 0 | 4-MeO phenyl | 2,4,6-$Cl_3$ phenyl | 191-3 (HCl) |
| — | $CH_2$ | 0 | 3,4-$Cl_2$ phenyl | 2,4,6-$Cl_3$ phenyl | 186-8 (HCl) |
| — | $CH_2$ | 0 | 3-MeO phenyl | 2,4-$Cl_2$ phenyl | 180-2 (HCl) |
| — | $CH_2$ | 0 | 2,4-$Cl_2$ phenyl | 2-Cl phenyl | 178-9 (HCl) |
| — | $CH_2$ | 0 | 4-F phenyl | 2-Cl phenyl | 179-181 (HCl) |
| — | $CH_2$ | 0 | 4-$NO_2$ phenyl | 2,4,6-$Cl_3$ phenyl | 185-8 (HCl) |
| — | $CH_2$ | 0 | 3-MeO phenyl | 2,6-$Cl_2$ phenyl | 186-8 (HCl) |
| — | $CH_2$ | 0 | 2,4-$Cl_2$ phenyl | 2,3,4,5,6-$F_5$ phenyl | 178-9 (HCl) |
| — | $CH_2$ | 0 | 4-Cl phenyl | 2,6-$Me_2$ phenyl | 168-170 (HCl) |
| — | $CH_2$ | 0 | 2,4-$Cl_2$ phenyl | 3,4-$Cl_2$ phenyl | 242-3 (HCl) |
| — | $CH_2$ | 0 | 4-F phenyl | 2,3-$Cl_2$ phenyl | 185-7 (HCl) |
| — | $CH_2$ | 0 | 2,5-$Cl_2$ phenyl | 2,6-$Cl_2$ phenyl | 205-8 (HCl) |
| — | $CH_2$ | 0 | 5-Me Thien-2-yl | 2,6-$Cl_2$ phenyl | 181-2 (HCl) |
| — | $CH_2$ | 0 | Thien-2-yl | 2,6-$Cl_2$ phenyl | 179-180 (HCl) |
| — | $CH_2$ | 0 | 2,4-$Cl_2$ phenyl | 3-$CF_3$ phenyl | 170-2 (HCl) |
| — | $CH_2$ | 0 | 4-CN phenyl | 2-Cl phenyl | 176-8 (HCl) |
| — | $CH_2$ | 0 | Phenyl | 2-Cl phenyl | 200-3 (HCl) |
| — | $CH_2$ | 0 | 4-$CF_3$ phenyl | 2,4-$Cl_2$ phenyl | 169-171 (HCl) |
| — | $CH_2$ | 0 | 2,6-$Cl_2$ phenyl | 2,4-$Cl_2$ phenyl | 202-4 (HCl) |
| — | $CH_2$ | 0 | Pyrid-2-yl | 2,6-$Cl_2$ phenyl | 212-4 (HCl) |
| — | $CH_2$ | 0 | 5-Br-Thien-2-yl | 2,4,6-$Cl_3$ phenyl | 155-8 (HCl) |
| — | CH (phenyl) | 0 | Phenyl | 2,4-$Cl_2$ phenyl | GUM |
| — | $CH_2$ | 0 | 3-Br phenyl | 2,6-$Cl_2$ phenyl | 179-182 (HCl) |
| — | $CH_2$ | 0 | 4-Cl phenyl | 3-$CF_3$ phenyl | 194-6 (HCl) |
| — | $CH_2$ | 0 | 2-F phenyl | 2,4,6-$Cl_3$ phenyl | 197-9 (HCl) |
| — | $CH_2$ | 0 | Thien-3-yl | 2,6-$Cl_2$ | 183-5 |

TABLE I-continued

| $Alk^1$ | $Alk^2$ | m | Ar | $Ar^1$ | m.p. (°C.) |
|---|---|---|---|---|---|
| | | | | phenyl | (HCl) |
| — | $CH_2$ | 0 | Naphth-2-yl | 2,4-$Cl_2$ phenyl | 183-5 (HCl) |
| — | $CH(CH_3)$ | 0 | Phenyl | 2,6-$Cl_2$ phenyl | 160-1 $[(HOOC)_2]$ |
| — | $CH(CH_3)$ | 0 | 4-F phenyl | 2,4-$Cl_2$ phenyl | 186-7 (HCl) |
| — | $CH_2$ | 0 | 4,5-$Br_2$ Thien-2-yl | 2,4-$Cl_2$ phenyl | 198-9 (HCl) |
| — | $CH(CH_2CH_2CH_3)$ | 0 | Phenyl | 2,4,6-$Cl_3$ phenyl | 130-2 $[(COOH)_2]$ |
| — | $CH[CH_2$(2,4-$Cl_2$ phenyl)] | 0 | 4-Cl phenyl | 2,6-$Cl_2$ phenyl | 152-3 |
| — | $CH_2$ | 0 | 3-Br phenyl | 2,4-$Cl_2$ phenyl | 159-161 (HCl) |
| — | $CH(CH_3)$ | 0 | 4-$F_3C$ phenyl | 2,6-$Cl_2$ phenyl | 120-2 $[(HOOC)_2]$ |
| — | $CH(CH_3)$ | 0 | 4-$F_3C$ phenyl | 2,4-$Cl_2$ phenyl | 143-6 $[(HOOC)_2]$ |
| — | $CH(CH_2CH_2CH_3)$ | 0 | Phenyl | 2,6-$Cl_2$ phenyl | 158-160 $[(HOOC)_2]$ |
| — | $CH(CH_2CH_2CH_3)$ | 0 | Phenyl | 2,4-$Cl_2$ phenyl | 79-81 $[(HOOC)_2]$ |
| — | $CH(CH_3)$ | 0 | 5-Cl Thien-2-yl | 2,4-$Cl_2$ phenyl | 136-8 (HCl) |
| — | $CH(CH_3)$ | 0 | 4-$F_3C$ phenyl | 2,4,6-$Cl_3$ phenyl | 114-116 $[(HOOC)_2]$ |
| — | $CH(CH_3)$ | 0 | Phenyl | 2,4-$Cl_2$ phenyl | 113-115 |
| — | $CH_2$ | 0 | Benzofuran-2-yl | 2,4-$Cl_2$ phenyl | 199-201 (HCl) |
| — | $CH_2$ | 0 | 2-Pyridyl | 2,4-$Cl_2$ phenyl | 222-4 (HCl) |
| — | $CH_2$ | 0 | 4-Cl phenyl | 3-MeO phenyl | 209-11 (HCl) |
| — | $CH_2$ | 0 | 2-Pyridyl | 2,4,6-$Cl_3$ phenyl | 215-6 (HCl) |
| — | $CH(CH_2CH_3)$ | 0 | Phenyl | 2,4,6-$Cl_3$ phenyl | 127-9 |
| — | $C(CH_3)_2$ | 0 | 4-Cl phenyl | 2,4,-$Cl_2$ phenyl | 146-7 (HCl) |
| — | $CH(CH_3)$ | 0 | 3,4-$Br_2$ Thien-2-2yl | 2,4-$Cl_2$ phenyl | 160-1 (HCl) |
| — | $CH_2$ | 0 | 5-Br Thien-2-yl | 2,4-$Cl_2$ phenyl | 194-5 (HCl) |
| — | $CH[CH_2$(2,4-$Cl_2$ phenyl)] | 0 | 4-Cl phenyl phenyl | 2,4-$Cl_2$ | 130-132 |
| — | $CH(CH_3)$ | 0 | Phenyl | 2,4,6-$Cl_3$ phenyl | 131-3 $[(COOH)_2]$ |
| $CH_2$ | $CH_2$ | 1 | 4-Cl phenyl | 2,4-$Cl_2$ phenyl | 151-3 (HCl) |
| — | $CH(CH_2CH_3)$ | 0 | Phenyl | 2,4-$Cl_2$ phenyl | 128 $[(COOH)_2]$ |
| — | $CH(CH_2CH_2CH_2CH_3)$ | 0 | 4,5-$Br_2$-thien-2-yl | 2,4-$Cl_2$ phenyl | 148-150 (HCl) |

For purposes of exemplification, certain compounds according to the present invention were tested to demonstrate the anti-fungal activity thereof by oral, topical and intravenous administration to test animals and in vitro, as compared to the activity of known anti-fungal agents. Several of the present compounds proved to possess outstanding efficacy against both Candida and dermatophyte infection by either oral, intravenous or topical administration.

The number preceding the name of the compound tested is the reference number used by us, and is retained as a matter of convenience.

HC274-(E)-1-(4-chlorophenyl)-2-(1H-imidazol-1-yl)ethanone, 2,4-dichlorophenylhydrazone, hydrochloride.

HC278-1-(4-chlorophenyl)-2-(1H-imidazol-1-yl)ethanone, 2,4-dichlorophenylhydrazone, nitrate HC316-1-(2-Chlorophenyl)-2-(1H-imidazol-1-yl)ethanone, 2,4-dichlorophenylhydrazone, hydrochloride.

HC344-(Z)-1-(4-chlorophenyl)-2-(1H-imidazol-1-yl) ethanone, 2,6-dichlorophenylhydrazone, hydrochloride.

HC390-(E)-1-(5-chlorothienyl-2-yl)-2-(1H-imidazol-1-yl)ethanone, 2,6-dichlorophenylhydrazone, hydrochloride.

HC415-(Z)-1-(4-chlorophenyl)-2-(1H-imidazol-1-yl)ethanone, 2,3,4,5,6-pentafluorophenylhydrazone hydrochloride.

Miconazole

1-[2-(2,4-Dichlorophenyl)-2-[(2,4-dichlorophenyl)methoxy]ethyl]-1H-imidazole.

Tioconazole

1-[2-[(2-Chloro-3-thienyl)methoxy]-2-(2,4-dichlorophenyl) ethyl]-1H-imidazole.

Ketoconazole cis-1-Acetyl-4-[4-[[2-(2,4-dichlorophenyl)-2-(1H-imidazol-1-yl-methyl)-1,3-dioxolan-4-yl]methoxy]-piperazine.

Clotrimazole 1-(2-Chlorophenyl)diphenylmethyl-1H-imidazole

Effect of HC274, Miconazole and Tioconazole on the recovery of viable candida cells from the kidneys of infected mice. Mice receive $25\times10^4$ cells of *C. albicans* i.v. Treatments (25 mg/kg) administered in PEG/Dextrose 1 h and 24 h after infection. Animals sacrified 48 h after infection and kidneys excised, weighed, homogenized and decimal dilutions spread on glucose-peptone agar.

| | No. of CFU/g kidney at 48 h | |
|---|---|---|
| Treatment | p.o. | i.v. |
| Control | $2.4\times10^5$ | $2.4\times10^5$ |
| HC 274 | $3.3\times10^3$ | $9\times10^2$ |
| Miconazole | $1.4\times10^3$ | $9\times10^2$ |
| Tioconazole | $2.2\times10^3$ | $1.2\times10^3$ |

CFU = colony forming units.

Effect of intravenous administration of HC274 and Tioconazole at 25 mg/ml on the recovery of viable candida cells from the kidneys of infected mice.

| Treatment | CFU/g kidney | % of control |
|---|---|---|
| HC274 | $7.7\times10^3$ | 52 |
| Tioconazole | $8.1\times10^3$ | 55 |
| Control | $14.7\times10^3$ | 100 |

Effect of oral treatment with HC274, HC316, HC390, HC415 and Ketoconazole on the recovery of viable candida albicans from the kidneys of infected mice.

| | Recovery of *C.albicans* (as percentage of control) | |
|---|---|---|
| Dose | 20 mg/kg | 5 mg/kg |
| HC274 | 47.8 | 84.2 |

-continued

| Dose | Recovery of *C.albicans* (as percentage of control) | |
|---|---|---|
| | 20 mg/kg | 5 mg/kg |
| HC390 | 41.1 | 57.3 |
| HC316 | 46.5 | 56.2 |
| HC415 | 17.2 | 14.0 |
| Ketoconazole | 11.7 | 51.0 |

Effect of oral or topical administration of HC274 and ketoconazole on vaginal candida infection in rats. Clearance of *C. albicans from rat vagina following oral or topical treatment (as percentage of control).*

Topical: HC274 95.5 Ketoconazole 99.9 Clotrimazole 100

| Oral: | | |
|---|---|---|
| HC274 20 mg/kg | HC274 10 mg/kg | Ketoconazole 10 mg/kg |
| 91.3 | 94.3 | 99.9 |

Topical treatment: 1% solution in polyethylene glycol administrated twice daily for 3 days.

Oral treatment: Once daily for 3 days.

Effect of oral or topical administration of HC274, HC344, Clotrimazole, and Ketoconazole on experimental Trichophyton mentagrophytes infection in guinea pigs.

| | Disease rating* Days after infection | |
|---|---|---|
| | 5 | 10 |
| Control | 100 | 68.0 |
| Clotrimazole (t) | 100 | 51.9 |
| HC274 (40 mg/kg p.o.) | 100 | 46.9 |
| HC274 (t) | 100 | 35.4 |
| HC344 (t) | 100 | 24.6 |
| Ketoconazole (20 mg/kg p.o.) | 100 | 63.7 |
| Ketoconazole (t) | 100 | 56.4 |

*Based on degree of hair loss, erythema, desquamation, Max. = 100 Treatments administered in Carbopol ® gel, once daily days 5-10.
All drugs at 1% w/w.
(t) = topical administration;
(p.o.) = oral administration.

The anti-bacterial activity of the compound HC274 according to the present invention was also compared with the activity of known anti-bacterial agents with the following results:

Anti-bacterial activity of HC274

| Organism | Zone diameter (MM) given by 50 μg of drug | | | |
|---|---|---|---|---|
| | HC274 | AMP | NA | PM |
| *Staphylococcus aureus* | 8 | 21 | 9 | 7 |
| *Streptococcus pyrogenes* | 9 | 25 | 0 | 0 |
| *Nocardia brasiliensis* | 12 | 38 | 7 | 0 |
| *Nocardia asteroides* | 11 | 38 | 0 | 11 |
| *pseudomonas aeruginosa* | 0 | 0 | 7 | 10 |
| *Proteus vulgaris* | 0 | 28 | 25 | 12 |
| *Klebsiella pneumoniac* | 0 | 11 | 21 | 10 |
| *Escherichia coli* | 0 | 17 | 18 | 10 |

AMP = Ampicillin
NA = Nalidixic Acid
PM = Polymyxin

Furthermore, the toxicity of compound HC274 according to the present invention was measured and compared with values obtained for known anti-fungal agents. The results, obtained by conventional procedures, were as follows:

7 day acute toxicity in male mice
Comparison of oral and i.v. toxicity of
HC274, HC344, HC390 and known anti-fungal agents

| Compound | $LD_{50}$ (mg/kg) i.v. | $LD_{12.5}$ (mg/kg) p.o. |
|---|---|---|
| HC274 | 85 | 440 |
| Miconazole | 80 | >500 |
| Tioconazole | 188 | >500 |
| Amphotericin B | 4 | 280 |
| Clotrimazole | 10 | 500 |
| 5-Fluorocytosine | 500 | 500 |
| HC344 | 780 (i.p.) | >1500 |
| HC390 | 610 (i.p.) | >1500 |

The activity of HC274 against anaerobic bacteria is shown in tests against the following strains of anaerobic bacteria (ATCC—American type culture collection; API—American petroleum institute):

| | | |
|---|---|---|
| *Clostridium sporogenes* | ATCC | 19404 |
| *Bacteroides fragilis* | ATCC | 23745 |
| *Bacteroides uniformis* | ATCC | 8492 |
| *Desulfovibrio desulfuricans* | API- | CORE |
| *Desulfovibrio desulfuricans* | API- | BREWER |
| *Desulfovibrio desulfuricans* | API- | SW2 |

The first three organisms are representative of species that are pathogenic in man. The D. desulfuricans strains represent a type of microorganism that causes serious problems in the recovery of oil and gas.

The tests were conducted by mixing a series of decreasing amounts of HC274 with a liquid nutrient medium that had been inoculated with one of the test organisms. These preparations were incubated for 24 hours at 37° C. and were then examined for the presence of growth as indicated by turbidity in the liquid medium. Results were recorded as the lowest concentrations, in mg/1, of HC274 that prevented growth of the test organisms (minimal inhibitory concentrations). Each test was run three times. The results are tabulated below.

Minimal Inhibitory Concentrations of HC274 (mg/l)

| Organism | Test HC274 | | | Metronidazole | | |
|---|---|---|---|---|---|---|
| | 1 | 2 | 3 | 1 | 2 | 3 |
| *C. sporogenes* ATCC 19404 | 2.5 | 2.5 | 7.5 | 0.5 | 0.25 | 0.75 |
| *B. fragilis* ATCC 23745 | 2.5 | 5.0 | 7.5 | 0.75 | 0.75 | 0.5 |
| *B. uniformis* ATCC 8492 | 2.5 | 2.5 | 5.0 | 0.5 | 0.25 | 0.25 |
| *D. desulfuricans* API-CORE | 0.75 | 1.0 | 1.0 | 0.5 | 0.25 | 0.25 |
| *D. desulfuricans* API-BREWER | 0.75 | 1.0 | 0.5 | 0.5 | 0.5 | 0.5 |
| *D. desulfuricans* API-SW2 | 1.0 | 1.0 | 1.0 | 0.25 | 0.25 | 0.25 |

The activity of the compounds identified in the Table II below was tested for antianaerobic activity against one strain of *Bacteroides fragilis,* one strain of *Bacteroides uniformis,* one strain of *Clostridium sporogenes* and one strain of *Trichomonas vaginalis* as the test organism. The methods used involved determining the minimum inhibitory concentration by the standard broth dilution method. The values for metronidazole (2-methyl-5- nitro-1H-imidazole-1-ethanol) are given above for reference purposes. For convenience the compounds are referred to by an internal reference number (an HC number) and this is correlated with the number of the Example wherein its production is described. The results obtained show that the compounds of the invention have high activity.

The compounds are also active against *Clostridium perfringens* as demonstrated in similar tests to those conducted for HC274. The results for HC316 and HC390 are shown below:

| Minimal Inhibitory Concentrations of HC316 and HC390 (mg/l) against *C. perfringens* (ATCC 13124) | | | |
|---|---|---|---|
| | HC316 | HC390 | Metronidazole |
| MIC(mg/l) | 0.8 | 3.1 | 0.3 |

TABLE II

| Compound Test Ref. No. Ex. No. | Minimal Inhibitory Concentration (MIC mg/l) *C. sporogenes* ATCC 19404 | *B. fragilis* ATCC 23745 | *B. uniformis* ATCC 8492 | T. vaginalis ATCC 30001 |
|---|---|---|---|---|
| HC-274 1 | 2.5 | 2.5 | 2.5 | 5 |
| 2 | 2.5 | 5 | 2.5 | 7.5 |
| (1) 3 | 7.5 | 7.5 | 5 | >10 |
| HC-306 1 | 10 | 10 | 10 | 50 |
| 2 | 2.5 | 2.5 | 2.5 | 50 |
| (24(b)) 3 | 2.5 | 2.5 | 2.5 | 25 |
| HC-316 1 | 1 | 2.5 | 2.5 | 50 |
| 2 | 2.5 | 2.5 | 2.5 | 50 |
| (12(c)) 3 | 2.5 | 2.5 | 2.5 | 50 |
| HC-363 1 | 2.5 | 1 | 2.5 | 50 |
| 2 | 2.5 | 2.5 | 2.5 | 50 |
| (24(e)) 3 | 7.5 | 2.5 | 2.5 | 50 |
| HC-364 1 | 10 | 10 | 10 | 50 |
| 2 | 5 | 2.5 | 2.5 | 50 |
| (25(c)) 3 | 25 | 5 | 2.5 | 50 |
| HC-378 1 | 50 | 10 | 10 | >50 |
| 2 | 25 | 2.5 | 2.5 | >50 |
| (24(a)) 3 | 25 | 2.5 | 5 | 50 |
| HC-380 1 | 10 | 10 | 10 | 50 |
| 2 | 2.5 | 2.5 | 2.5 | 25 |
| (24(d)) 3 | 2.5 | 2.5 | 2.5 | 25 |
| HC-390 1 | 2.5 | 5 | 2.5 | >50 |
| 2 | 5 | 2.5 | 2.5 | >50 |
| (5) 3 | 7.5 | 2.5 | 2.5 | >50 |
| HC-403 1 | 1 | 5 | 2.5 | <50 |
| 2 | 7.5 | 2.5 | 2.5 | 7.5 |
| (25(f)) 3 | 50 | 5 | 2.5 | <50 |
| HC-420 1 | 10 | 10 | 10 | 50 |
| 2 | 2.5 | 2.5 | 1 | 50 |
| (28(a)) 3 | 2.5 | 2.5 | 2.5 | 50 |
| HC-433 1 | 1 | 1 | 0.5 | 75 |
| 2 | 2.5 | 2.5 | 5 | 50 |
| (24(f)) 3 | 2.5 | 2.5 | 2.5 | 50 |
| HC-438 1 | 2.5 | 5 | 5 | 25 |
| 2 | 7.5 | 7.5 | 5 | 50 |
| (25(1)) 3 | 2.5 | 5 | 5 | 75 |
| HC-442 1 | 5 | 2.5 | 2.5 | 50 |
| 2 | 2.5 | 5 | 5 | 75 |
| (27(a)) 3 | 2.5 | 5 | 5 | 100 |
| HC-464 1 | 2.5 | 2.5 | 2.5 | 10 |
| 2 | 5 | 5 | 2.5 | 50 |
| (26(a)) 3 | 2.5 | 5 | 2.5 | 50 |
| HC-466 1 | 5 | 1 | 1 | 50 |
| 2 | 5 | 5 | 5 | 50 |
| (25(a)) 3 | 5 | 5 | 5 | 50 |
| HC-469 1 | 2.5 | 5 | 5 | 50 |
| 2 | 7.5 | 5 | 1 | 75 |
| (26(b)) 3 | 1 | 10 | 2.5 | 100 |
| HC474 1 | 7.5 | 5 | 10 | |
| 2 | 5 | 7.5 | 5 | 50 |
| (25(m)) 3 | 5 | 7.5 | 7.5 | 50 |
| HC-482 1 | 5 | 5 | 2.5 | 25 |
| 2 | 5 | 5 | 2.5 | 25 |
| (28(d)) 3 | 5 | 5 | 2.5 | 25 |
| HC-486 1 | 2.5 | 5 | 2.5 | 50 |

TABLE II-continued

| Compound Test Ref. No. Ex. No. | Minimal Inhibitory Concentration (MIC mg/l) *C. sporogenes* ATCC 19404 | *B. fragilis* ATCC 23745 | *B. uniformis* ATCC 8492 | T. vaginalis ATCC 30001 |
|---|---|---|---|---|
| 2 | 5 | 5 | 2.5 | 50 |
| (23) 3 | 5 | 5 | 5 | 75 |
| HC-506 1 | >50 | 5 | 5 | — |
| (27(d)) 2 | >50 | 5 | 2.5 | — |
| HC-507 1 | 2.5 | 2.5 | 5 | — |
| (31) 2 | 2.5 | 5 | 2.5 | — |
| HC-523 1 | 2.5 | 7.5 | 5 | 50 |
| 2 | 2.5 | 5 | 2.5 | 50 |
| (28(c)) 3 | 5 | 7.5 | 5 | 50 |
| HC-525 1 | 2.5 | 2.5 | 2.5 | 50 |
| 2 | 2.5 | 2.5 | 2.5 | 50 |
| (24(g)) 3 | 2.5 | 2.5 | 2.5 | 50 |
| HC-561 1 | 1 | 1 | 5 | >100 |
| 2 | 1 | 2.5 | 7.5 | >100 |
| (28(e)) 3 | 1 | 5 | 7.5 | >100 |

The compounds used according to the invention as anti-thrombotics were tested by the following method for their ability to inhibit platelet thromboxane generation.

Platelet rich plasma preparation

Human venous blood was collected from healthy male donors, who had denied any medication in the previous 14 days. Nine volumes of blood were mixed with one volume of 3.24% trisodium citrate. The citrated blood was centrifuged at 160 g for 10 mins. at 22° C. to obtain platelet rich plasma (PRP). The platelets were then counted on a Coulter counter, and the platelet count was adjusted to 200,000 per μl with plasma.

Thromboxane Generation

The PRP was then dispensed as aliquots into micro-Eppendorf tubes, maintained at 37° C. in a dry bath. The compounds dissolved either in saline, ethanol, or DMSO were added in duplicate to the PRP aliquots to produce final concentrations of 0.3, 3 and 30 μg/ml. When ethanol and DMSO were used as the vehicle, triplicate controls containing the same percentage of vehicle as the test compounds were made. The final concentration or organic solvent was never more than 0.1%, which in previous experiments had no effect on $TxB_2$ generation.

Following a 10 min. incubation with test compounds or vehicle, collagen was added to produce a final concentration of 8 μg/ml. The tubes were then whirly-mixed for 15 seconds and replaced in the dry bath for a further 10 minutes, controls received saline instead of collagen. The reaction was then stopped by rapid centrifugation, 15,000 g for 3 mins. The plasma was removed and frozen at −29° C. until assayed.

Assay of Thromboxane $B_2$

Briefly, 100 μl aliquots, in tricine buffered saline+0.8% gelatin (pH 8.0) of the following were incubated together for 1 hour at 37° C.: thromboxane Tx $B_2$ (plasma extract, spiked plasma extract or standards 20 to 20,000 pg/ml), $^3H$—$TxB_2$ (approximately 15,000 dpm) and anti-$TxB_2$ antiserum (0.5 μg/100 μl). The free and protein bound $^3H$—$TxB_2$ were separated by ammonium sulphate precipitation followed by centrifugation. 300 μl of the supernatant was added to an aqueous scintillation fluid, and the radioactivity present was counted in a liquid scintillation counter. The binding of $^3H$—$TxB_2$ in the absence of added $TxB_2$ was approximately 55%. The least amount of $TxB_2$ to be detected accurately in the plasma was 0.08 ng/ml. Cross reactivity with other prostaglandins is less than 0.005% except $PGD_2$ which is 1%.

Thus plasma samples were assayed to give a rough approximation of $TxB_2$ content. The plasma was then appropriately diluted and assayed in duplicate to give accurate values.

Analysis of Results

The amount of $TxB_2$ generated by the collagen was calculated by subtracting mean values obtained for the saline stimulated platelets from the mean values obtained from the collagen stimulated platelets. Then the amount of $TxB_2$ generated in the presence of each concentration of compound was expressed as a % control and dose response curves were then constructed to determine the concentration of compound which produced a 50% inhibition. These values known as the $IC_{50}$ obtained for various compounds tested are given in table III below.

TABLE III

| Compound Ref. No. | Ex. No. | Activity $IC_{50}$ |
|---|---|---|
| HC 274 | 1 | 15.9 |
| HC 290 | 11 | 4.9 |
| HC 336 | 14(g) | 0.9 |
| HC 346 | 16(b) | 2.7 |
| HC 365 | 17 | 3.6 |
| HC 368 | 18 | 0.8 |
| HC 377 | 19 | 2.7 |
| HC 402 | 20 | 0.7 |
| HC 416 | 21 | 13.8 |
| HC 418 | 25(k) | 20.9 |
| HC 426 | 22 | 5.5 |
| HC 500 | 8 | >80 |
| HC 501 | 9 | <0.78 |

HC 501 has also been evaluated for platelet aggregation 3 hrs. after oral administration in the retired male breeder rat model (R. N. Saunders et al, Lab. Anim. Sci., 1977, 27, 757).

| Compound | $ED_{50}$ (3 hr. post oral administration) |
|---|---|
| HC 501 | 0.003 mg/kg |
| Aspirin | 7.7 mg/kg |
| Dipyridamide | 6.8 mg/kg |
| Sulfinpyrazone | 4.1 mg/kg |

Aspirin: 2-(Acetyloxy)benzoic acid.
Dipyridamide: 2,2',2'',2'''-[(4,8-Di-1-piperidinyl-pyrimido]5,4-d[pyrimidine-2,6-diyl)dinitrolo]tetrakisethanol.
Sulfinpyrazone: 1,2-Diphenyl-4-[2-(phenylsulfinyl)ethyl]-3,5-pyrazolidinedione.

EXAMPLE 32

Pharmaceutical Compositions.

(a) Tablets. The active imidazole compound (e.g. HC274) is ground to a fine powder, blended with starch and lactose, and moistened with water before granulation. The granule mass is then milled, blended with magnesium stearate and compressed into tablets. The amount of active ingredient used was such as to provide 50 mg of active ingredient per tablet.

(b) Creams. Creams may be prepared by dissolving an appropriate amount of the active ingredient (e.g. HC344) in Polyethylene Glycol 400 and then blending with Polyethylene Glycol 4000 in a 60:40 ratio. A suitable concentration of active ingredient in the cream is from 1 to 5%.

(c) Suppositories. A suppository may be made by dispensing the active ingredient (e.g. HC344) in a suitable molten base in an appropriate amount and allowing the mass to solidify in a mould.

We claim:

1. A compound of the formula

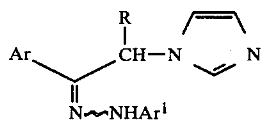

or a pharmacologically acceptable salt thereof wherein:
Ar is phenyl, thienyl or a mono, di or trisubstituted form thereof wherein the mono, di or trisubstituent is F, Cl, Br, $CF_3$, $C_1$–$C_3$alkyl, $C_1$–$C_3$alkoxy, CN, or $NO_2$;
$Ar^1$ is $C_6H_{5-n}X_n$;
X is F, Cl or $CF_3$;
R is H, $CH_3$ or $CH_2CH_3$; and
n is an integer from 1 to 5.

2. A compound according to claim 1 wherein $Ar^1$ is chloro or fluorophenyl, dichloro or difluorophenyl, 2,4,6-trichloro or trifluorophenyl, pentachloro or pentafluorophenyl, or trifluoromethylphenyl.

3. A compound according to claim 1 or 2 wherein Ar is phenyl, thienyl, chloro or fluorophenyl, di or tri (chloro or fluoro) phenyl, 2 or 4-methylphenyl, 2 or 4-methoxyphenyl, trifluoromethylphenyl, or cyanophenyl.

4. A compound according to claim 1 wherein Ar is 4-chlorophenyl and $Ar^1$ is 2,4-dichlorophenyl.

5. A compound according to claim 1 wherein Ar is 4-chlorophenyl and $Ar^1$ is 2,6-dichlorophenyl.

6. A compound according to claim 1 wherein Ar is 2-chlorophenyl and $Ar^1$ is 2,4-dichlorophenyl.

7. A compound according to claim 1 wherein Ar is 4-chlorophenyl and $Ar^1$ is pentafluorophenyl.

8. A compound according to claim 1 wherein Ar is 2,4-dichlorophenyl and $Ar^1$ is 2,4,6-trichlorophenyl.

9. A compound according to claim 1 wherein Ar is 4-chlorophenyl and $Ar^1$ is 2-chlorophenyl.

10. A compound according to claim 1 wherein Ar is 5-chlorothien-2-yl and $Ar^1$ is 2,6-dichlorophenyl.

11. A compound according to claim 1 wherein Ar is phenyl and $Ar^1$ is 2,4-dichlorophenyl.

12. (E)-1-(4-chlorophenyl)-2-(1H-imidazol-1-yl) ethanone, 2,4-dichlorophenylhydrazone, hydrochloride according to claim 1.

13. (Z)-1-(4-chlorophenyl)-2-(1H-imidazol-1-yl) ethanone, 2,6-dichlorophenylhydrazone, hydrochloride according to claim 1.

14. (E)-1-(5-chlorothienyl-2-yl)-2-(1H-imidazol-1-yl) ethanone, 2,6-dichlorophenylhydrazone, hydrochloride according to claim 1.

15. (Z)-1-(4-chlorophenyl)-1-(1H-imidazol-1-yl) ethanone, 2-chlorophenylhydrazone, hydrochloride according to claim 1.

16. 1-(2,4-dichlorophenyl)-2-(1H-imidazol-1-yl) ethanone, 2,4,6-trichlorophenylhydrazone, hydrochloride according to claim 1.

17. (Z)-1-(4-chlorophenyl)-2-(1H-imidazol-1-yl) ethanone, 2, 3, 4, 5,6-pentafluorophenylhydrazone, hydrochloride according to claim 1.

* * * * *